United States Patent
Mellul et al.

(10) Patent No.: US 7,316,814 B2
(45) Date of Patent: *Jan. 8, 2008

(54) COSMETIC COMPOSITION COMPRISING A SILICONE-CONTAINING COMPOUND AND A FATTY ACID ESTER

(75) Inventors: Myriam Mellul, L'Hay-les-Roses (FR); Pascal Arnaud, Creteil (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/434,359

(22) Filed: May 9, 2003

(65) Prior Publication Data

US 2004/0109837 A1    Jun. 10, 2004

Related U.S. Application Data

(63) Continuation of application No. 09/007,768, filed on Jan. 16, 1998, now abandoned, which is a continuation of application No. 08/592,511, filed on Jan. 26, 1996, now Pat. No. 5,738,841.

(30) Foreign Application Priority Data

Jan. 30, 1995   (FR) .................................. 95 01040

(51) Int. Cl.
*A61K 8/18*  (2006.01)
*A61K 8/00*  (2006.01)
*A61K 8/92*  (2006.01)
*A61K 8/02*  (2006.01)

(52) U.S. Cl. .................. 424/401; 424/63; 424/64; 424/70.7

(58) Field of Classification Search ............ 424/400, 424/401, 63, 64, 70.7
See application file for complete search history.

(56) References Cited

U.S. PATENT DOCUMENTS

| 5,034,216 A | * | 7/1991 | Barone et al. ............ 424/63 |
| 5,085,855 A | | 2/1992 | Shore |
| 5,116,604 A | * | 5/1992 | Fogel et al. ............... 424/59 |
| 5,393,526 A | * | 2/1995 | Castro .................... 424/401 |
| 5,425,939 A | * | 6/1995 | Guerrero et al. ......... 424/78.02 |
| 5,468,471 A | | 11/1995 | Zecchino et al. |
| 5,496,544 A | * | 3/1996 | Mellul et al. ............ 424/78.03 |
| 5,505,935 A | | 4/1996 | Guerrero et al. |
| 5,505,937 A | | 4/1996 | Castrogiovanni et al. |
| 5,547,659 A | | 8/1996 | Rinaldi et al. |
| 5,738,841 A | * | 4/1998 | Mellul et al. ............. 424/59 |

FOREIGN PATENT DOCUMENTS

| EP | 0 437 216 | 1/1991 |
| EP | 0 602 905 A2 | 6/1994 |
| JP | 62-169714 | 7/1987 |
| WO | WO93/17660 A1 * | 9/1993 |
| WO | WO 94/18940 | 9/1994 |

OTHER PUBLICATIONS

Hawley, G. G., "Definitive Rules for Nomenclature of Organic Chemistry," *The Condensed Chemical Dictionary*, Ninth Edition, 1977, Van Nostrand Reinhold Company, pp. C-1 to C-32, 449.

* cited by examiner

*Primary Examiner*—Sreeni Padmanabhan
*Assistant Examiner*—Marina Lamm
(74) *Attorney, Agent, or Firm*—Finnegan Henderson Farabow Garrett & Dunner, L.L.P.

(57) ABSTRACT

The present application relates to an anhydrous cosmetic composition comprising at least one silicone-containing compound and a specific fatty acid ester. This composition may be used as a care product and/or a make-up product for the skin and/or for keratinous materials.

17 Claims, No Drawings

COSMETIC COMPOSITION COMPRISING A SILICONE-CONTAINING COMPOUND AND A FATTY ACID ESTER

This is a continuation of application Ser. No. 09/007,768, filed Jan. 16, 1998, now abandoned, which is a continuation of application Ser. No. 08/592,511, filed Jan. 26, 1996, now U.S. Pat. No. 5,738,841 and claims benefit of priority of French application No. 95-01040, filed Jan. 30, 1995, all of which are incorporated herein by reference.

The present invention relates to a cosmetic composition that may be used as a make-up composition and/or a skincare composition comprising silicone-containing compounds such as silicone oils, gums and/or waxes, and optionally hydrocarbon compounds.

The use of silicone-containing compounds in cosmetic compositions, in particular make-up compositions, is known. These compounds make it possible to, inter alia, obtain a particularly homogeneous film on the skin, this film having good cosmetic properties. These compounds also make it possible to improve the staying power of the make-up on account of their hydrophobic nature.

It is also known to use hydrocarbon compounds in cosmetic compositions. However, it has been observed that certain silicone-containing compounds were incompatible with certain hydrocarbon compounds generally used in cosmetic compositions, which thus limited their use.

Various solutions have been proposed in order to allow the preparation of a cosmetic composition comprising both silicone-containing compounds and hydrocarbon compounds. Mention may be made, for example, of the use of hydrocarbon solvents or co-solvents such as isoparaffins; however, their odour and their volatility are not always appreciated.

Mention may also be made of Patent Application JP 62-169714, which describes a composition comprising a silicone oil and a solid fatty substance, in which it is necessary, on the one hand, to add during its preparation an ester oil with a solidification point equal to or above 0° C., this oil having a branched intramolecular structure consisting of a fatty acid and an alcohol, and, on the other hand, to treat the pigment charge with a methylhydrogenopolysiloxane.

Mention may also be made of Application EP 437,216, which describes agents for solubilizing and/or dissolving silicones, which are in the form of esters of formula $R_1COOR_2$ where $R_1$ is a $C_{4-17}$ isoalkyl and $R_2$ is a $C_{3-18}$ isoalkyl. However, when they are applied to the skin, the cosmetic compositions comprising these solubilizing agents give a particularly unpleasant sensation of dryness, in particular in the case of lipsticks.

The aim of the present invention is to propose a homogeneous cosmetic composition comprising at least one silicone-containing compound in combination with a hydrocarbon compound of high molecular mass.

The subject of the present invention is thus an anhydrous cosmetic composition comprising, in a fatty phase, at least one silicone-containing compound in combination with octyldodecyl neopentanoate.

It has in effect been found, surprisingly and unexpectedly, that such a composition is in homogeneous form, that is to say that, in the case of liquid/liquid mixtures, a homogeneous distribution of the constituents is observed, leading to a single-phase mixture, and that, in the case of solid/liquid mixtures, such as wax-in-oil mixtures, the formation of a homogeneous and clear mixture under hot conditions and the formation of a homogeneous dispersion of the wax in the oil upon cooling are observed.

The composition obtained has the advantage of possessing good cosmetic properties, and in particular does not give a dry sensation when it is applied to the skin.

Another advantage of the invention lies in the fact that other silicone-containing and/or hydrocarbon compounds, which are generally mutually incompatible, may be added to the fatty phase while at the same time keeping the composition homogeneous.

Another subject of the invention is the use of octyldodecyl neopentanoate as a compatibilizing agent in an anhydrous cosmetic composition comprising at least one silicone-containing compound.

In the present description, the expression compatibilizing agent is understood to refer to an agent which makes it possible to obtain a homogeneous composition as defined above.

Octyldodecyl neopentanoate is a $C_5$ neopentanoic acid ester of $C_{20}$ isoarachidyl alcohol. It has thus been found that this ester is an excellent agent for compatibilizing silicone-containing compounds with each other and/or silicone-containing compounds with hydrocarbon compounds. Furthermore, octyldodecyl neopentanoate has good thermal and chemical stability, and makes it possible to obtain compositions with a much oilier texture on application, in comparison with compositions of the prior art not containing it.

Finally, it has been found that octyldodecyl neopentanoate has noteworthy dispersant properties with respect to powders and makes it possible to obtain a homogeneous dispersion.

Thus, another subject of the invention is the use of this ester as an agent for aiding dispersion, in cosmetic compositions comprising powders, thus making it possible to obtain a homogeneous mixture in which the pulverulent particles are perfectly dispersed in the fatty phase.

Octyldodecyl neopentanoate may represent preferably 0.5-99% by weight, more preferably 1-70% by weight, of the fatty phase of the composition according to the invention.

The composition according to the invention may generally be in the form of a compacted or poured product, or alternatively in the form of a solid or liquid anhydrous greasy product.

It thus comprises a fatty phase in which are present octyldodecyl neopentanoate, at least one silicone-containing compound and optionally hydrocarbons, and possibly lipophilic or even hydrophilic additives, optionally together with a pulverulent phase comprising pigments and/or fillers.

The fatty phase may represent preferably 1-100% by weight of the final composition, and the pulverulent phase may represent preferably 0-99% by weight of the final composition.

The composition according to the invention thus comprises at least one silicone-containing compound which may be chosen from silicone oils, gums and/or waxes. Mention may be made in particular of cyclomethicones such as cyclomethicones D4, D5 and D6; polydimethylsiloxanes; alkyldimethicones; polyphenylmethylsiloxanes such as phenyldimethicones and phenyltrimethicones; and silicones modified with aliphatic and/or aromatic groups, which optionally contain fluorine, or with functional groups such as hydroxyl, thiol and/or amine groups. Mention may also be made of the silicones of formula (I):

$$X-\underset{R_2}{\overset{R_1}{\underset{|}{\overset{|}{Si}}}}-O-\left[\underset{R_4}{\overset{R_3}{\underset{|}{\overset{|}{Si}}}}-O\right]_n-\left[\underset{R_6}{\overset{R_5}{\underset{|}{\overset{|}{Si}}}}-O\right]_p-\underset{R_2}{\overset{R_1}{\underset{|}{\overset{|}{Si}}}}-X$$

in which:

$R_1$, $R_2$, $R_5$ and $R_6$ independently represent an alkyl radical having 1 to 6 carbon atoms, $R_3$ and $R_4$ independently represent an alkyl radical having from 1 to 6 carbon atoms or an aryl radical, X is an alkyl radical having from 1 to 6 carbon atoms, a hydroxyl radical or a vinyl radical, n and p being chosen so as to impart to the silicone-containing compound a viscosity of greater than 100,000 mPa s, preferably of greater than 500,000 mPa s, and possibly ranging up to 1,000,000 mPa s.

The composition according to the invention may also comprise hydrocarbon compounds such as plant, animal, mineral and/or synthetic oils or waxes.

Mention may be made of liquid paraffin, liquid petrolatum, perhydrosqualene, arara oil, sweet almond oil, calophyllum oil, avocado oil, sesame oil, castor oil, jojoba oil, olive oil or cereal germ oil. It is also possible to use esters of lanolic acid, of oleic acid, of lauric acid, of stearic acid or of myristic acid for example; alcohols such as oleyl alcohol, linoleyl alcohol or linolenyl alcohol, isostearyl alcohol or octyldodecanol; acetyl glycerides, alcohol or polyalcohol octanoates, decanoates, or ricinoleates, caprylic/capric triglycerides or $C_{10}$ to $C_{18}$ fatty acid triglycerides.

It is also possible to use hydrogenated oils which are solid at 25° C., such as hydrogenated castor oil, palm oil or coconut oil, or hydrogenated tallow; mono- di- tri- or sucroglycerides; lanolins; and fatty esters which are solid at 25° C. Among the waxes, mention may be made of animal waxes such as beeswax; plant waxes such as carnauba wax, candellila wax, ouricurry wax, Japan wax or waxes from cork fibres or from sugar cane; mineral waxes, for example paraffin wax, lignite wax, microcrystalline waxes or ozokerites; synthetic waxes and among these polyethylene waxes and waxes obtained by Fischer-Tropsch synthesis.

The composition may also comprise pigments and/or fillers usually used in such cosmetic compositions.

The pigments may be white or coloured, inorganic, organic and/or pearlescent. Mention may be made, without any limiting nature, of titanium dioxide, zinc oxide, zirconium dioxide, black, yellow, red and brown iron oxides, cerium dioxide, chromium oxide, ferric blue, carbon black, barium, strontium, calcium and aluminium lakes, and mica coated with titanium oxide or with bismuth oxychloride.

The fillers may be inorganic, organic or synthetic, lamellar or non-lamellar, and spherical or non-spherical. Mention may be made of talc, mica, silica, kaolin, Nylon and polyethylene powders, Teflon, starch, titanium mica, natural mother of pearl, boron nitride, hollow microspheres such as Expancel from Nobel Industrie, and silicone resin microbeads.

The composition according to the invention may also comprise constituents usually used in cosmetic compositions of this type.

These constituents are preferably chosen according to the desired cosmetic effect for the final composition, such as covering power, transparency, the mattness and/or the satiny appearance. Mention may be made, without any limiting nature, of:

gelling agents such as the modified clays known under the name of bentone, which are sold by the company NL Industrie and are used as such or preprocessed in a gel; hydrophobic silica; fatty salts of aluminium.

vitamins such as tocopherols and derivatives thereof, vitamin A and derivatives thereof, vitamin C and derivatives thereof such as fatty esters including the palmitate.

sunscreens such as octyl methoxycinnamate (Parsol MCX), 3-benzophenone (Uvinul M40) and butylmethoxydibenzoylmethane (Parsol 1789).

oily materials such as fragrances, essential oils and fluoro oils.

wetting agents such as propylene glycol and glycerol.

The hydrophilic constituents are preferably dispersed in the fatty phase.

The processes for the manufacture of the compositions according to the invention differ in no way from the processes conventionally used in cosmetics which are entirely familiar to those skilled in the art.

The compositions according to the invention may be in the form of a care product and/or a make-up product for the skin and/or keratinous materials.

This product may be in the form of a free, poured or compacted powder (foundation, blusher or eyeshadow), a more or less fluid anhydrous greasy product (lipstick, mascara or solvent varnish), an oil or lotion for the body and/or the face, or even a hair product such as an anhydrous styling gel.

The invention will now be described in greater detail by means of the following examples, which are given solely by way of illustration and in no way limit the invention, and in which the percentages are given by weight.

EXAMPLES

Example 1

The solubility of an oil and a silicone gum in the ester according to the invention and in esters of the prior art, of similar chemical structure, was compared. The silicone oil is a PDMS of viscosity 350 mPa s (DC200 oil from Dow Corning).

The silicone gum is a gum of formula (I) in which the substituents R1 to R6 and X represent a methyl group, p=0 and n=2300, of viscosity 500,000 mPa s (AK 500,000 from Wacker).

The following results were obtained:

|  | Number of carbon atoms | Silicone oil | Silicone gum |
| --- | --- | --- | --- |
| Octyldodecyl neopentanoate (Elefac 1-205 from Bernel Chemical) | 20 + 5 | ∞ | ∞ |
| Isostearyl neopentanoate (Ceraphyl 375 from ISP) | 18 + 5 | 0 | 0 |
| 2-hexyldecyl isononanoate (Stéarineries Dubois) | 16 + 9 | 0 | 0 |
| Isostearyl isononanoate (Lanol 189 from SEPPIC) | 18 + 9 | 0 | 0 |

∞: excellent solubility of the oil and of the gum in the ester considered was found, in all proportions.
0: no solubility of the oil or of the gum in the ester considered was found.

Octyldodecyl neopentanoate makes it possible to obtain a homogeneous composition comprising the ester considered and a particular silicone oil or a particular silicone gum, whereas esters of similar chemical structure do not allow this.

Example 2

The maximum mass content of ester which may be added, at 25° C., to a solution of gum in a silicone oil without observing precipitation of the gum was measured.

The test solution comprised a gum of formula (I) in which the substituents R1 to R6 represent a methyl group, the substituent X represents a hydroxyl group, p=0 and n=2,700, as a 13% solution in polydimethylsiloxane (Q2-1403 from Dow Corning).

The following results were obtained:

| | |
|---|---|
| Octyldodecyl neopentanoate (Elefac I-205 from Bernel Chemical) | no precipitation up to at least 1000% |
| Isostearyl neopentanoate (Cheraphyl 375 from ISP) | 68% |
| 2-hexyldecyl isononanoate (Stéarineries Dubois) | 72% |
| Isostearyl isononanoate (Lanol 189 from SEPPIC) | 60% |

It was found that octyldodecyl neopentanoate makes it possible to solubilize a particular gum virtually infinitely, whereas esters of similar chemical structure do not allow this.

Example 3

The correct compatibility (solubility) of octyldodecyl neopentanoate with several silicone-containing compounds of different chemical structure was observed.

The following results were obtained:

| | |
|---|---|
| Silicone oil(PDMS) DC200 from Dow Corning 350 mPa s | ∞ |
| Phenyltrimethicone BELSIL PDM 1000 from Wacker | ∞ |
| Diphenyldimethicone Gum 761 from Rhône Poulenc | greater than 10% |
| Alkyldimethicone D2 5519 from Dow Corning | ∞ |
| Fluorodimethicone GRANSIL DM 100 from Grant | ∞ |
| Amodimethicone L656 from Wacker | ∞ |
| Hydroxylated silicone SILBIONE 71516V60 from Rhône Poulenc | ∞ |
| PDMS + trimethyl siloxysilicate mixture (67/33) DC593 from Dow Corning | ∞ |

∞: excellent solubility of the silicone-containing compound in the ester was found, in all proportions.

Octyldodecyl neopentanoate thus has a certain compatibility with a large number of silicone-containing compounds of diverse chemical structures.

Example 4

A mixture was prepared comprising:

30% of PDMS+trimethyl siloxysilicate mixture (DC593 from Dow Corning)

30% of alkyldimethicone (ABIL WAX 9801 from Goldschmidt) and

40% of octyldodecyl neopentanoate

A homogeneous solution was obtained, whereas, in the absence of octyldodecyl neopentanoate, an inhomogeneous mixture of the constituents was observed, macroscopically and microscopically. Octyldodecyl neopentanoate may thus be used as a co-solvent for silicones which are mutually incompatible.

Example 5

A lipstick was prepared comprising:

| | |
|---|---|
| octyldodecyl neopentanoate | 60% |
| diphenyldimethicone (Gum 761 from Rhône Poulenc) | 0.1% |
| polyethylene wax | 13.5% |
| microcrystalline wax | 4.5% |
| arachidyl propionate | 10% |
| pigments | 11.9% |

The silicone gum was dissolved in the octyldodecyl neopentanoate at 80° C. After homogenization, the other constituents were added, at 95° C.

After stirring and grinding, the mixture was poured, at 95° C., into alveoli so as to obtain a lipstick having good cosmetic properties. In particular, no dry sensation on the lips is reported on application of the lipstick, this being an advantageous sensory aspect of the composition according to the invention.

Example 6

A lipstick was prepared comprising:

| | |
|---|---|
| octyldodecyl neopentanoate | 65% |
| alkyldimethicone (D2 5519 from Dow Corning) | 5% |
| polyethylene wax | 13.5% |
| microcrystalline wax | 4.5% |
| pigments | 12% |

The constituents were all mixed together at 95° C.

After homogenization and grinding, the mixture was poured, at 95° C., into alveoli so as to obtain a lipstick having good cosmetic properties.

Example 7

An eyeshadow was prepared having the following composition:

Pulverulent Phase

| | |
|---|---|
| talc | 48% |
| titanium mica | 30% |
| chromium oxide | 8% |
| zinc oxide | 2% |

Fatty Phase

| | |
|---|---|
| octyldodecyl neopentanoate | 10% |
| gum + oil mixture (Q2-1403 from Dow Corning) | 2% |

The constituents of the pulverulent phase were mixed together, the fatty phase was then added and the fixture was stirred, sieved and compacted into a metal shell.

An eyeshadow having good cosmetic properties was obtained.

Example 8

A face powder was prepared having the following composition:

Pulverulent Phase

| talc | 61% |
|---|---|
| mica | 20% |
| Nylon powder | 6% |
| iron oxide | 7% |

Fatty Phase

| octyldodecyl neopentanoate | 2.4% |
|---|---|
| dimethicone | 3.6% |

By the same procedure as in Example 7, a compacted face powder having good cosmetic properties was obtained.

We claim:

1. A homogeneous anhydrous make-up cosmetic composition comprising a fatty phase which comprises at least one silicone-containing compound and octyldodecyl neopentanoate, wherein said composition is in a form chosen from foundations, mascaras, and lip compositions.

2. The homogeneous anhydrous make-up cosmetic composition according to claim 1, wherein said at least one silicone-containing compound is chosen from polydimethylsiloxanes; alkyldimethiocones; polyphenylmethylsiloxanes; silicones modified with at least one group chosen from aliphatic groups and aromatic groups, which groups may contain fluorine; silicones modified with at least one group chosen from hydroxyl groups, thiol groups, and amine groups; and silicones of formula (I):

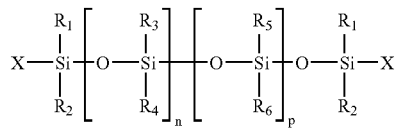

in which:
R₁, R₂, R₅ and R₆ independently are chosen from alkyl radicals having from 1 to 6 carbon atoms,
R₃ and R₄ independently are chosen from alkyl radicals having from 1 to 6 carbon atoms and aryl radicals,
X is chosen from alkyl radicals having from 1 to 6 carbon atoms, a hydroxyl radical and vinyl radicals, and
wherein n and p are chosen so as to impart to the silicone-containing compound a viscosity of greater than 100,000 mPa s.

3. The homogeneous anhydrous make-up cosmetic composition according to claim 2, wherein said at least one silicone-containing compound is a polydimethylsiloxane chosen from cyclotetrasiloxane, cyclopentasiloxane, and cyclohexasiloxane.

4. The homogeneous anhydrous make-up cosmetic composition according to claim 2, wherein said at least one silicone-containing compound is a polyphenylmethylsiloxane chosen from phenyldimethicones and phenyltrimethicones.

5. The homogeneous anhydrous make-up cosmetic composition according to claim 2, wherein said at least one silicone-containing compound is chosen from said silicones modified with at least one group chosen from hydroxyl groups, thiol groups, and amine groups.

6. The homogeneous anhydrous make-up cosmetic composition according to claim 1, wherein said at least one silicone-containing compound is chosen from the silicones of formula (I):

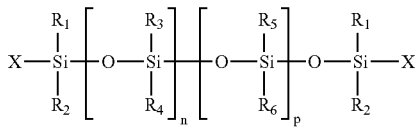

in which:
R₁, R₂, R₅ and R₆ independently are chosen from alkyl radicals having from 1 to 6 carbon atoms,
R₃ and R₄ independently are chosen from alkyl radicals having from 1 to 6 carbon atoms and aryl radicals,
X is chosen from alkyl radicals having from 1 to 6 carbon atoms, a hydroxyl radical and vinyl radicals, and
n and p being chosen so as to impart to the silicone-containing compound a viscosity of greater than 100,000 mPa s.

7. The homogeneous anhydrous make-up cosmetic composition according to claim 1, further comprising a pigment.

8. The homogeneous anhydrous make-up cosmetic composition according to claim 1, further comprising at least one wax.

9. The homogeneous anhydrous make-up cosmetic composition according to claim 1, wherein said octyldodecyl neopentanoate is present in an amount sufficient to function as a compatibilizing agent for said composition.

10. The homogeneous anhydrous make-up cosmetic composition according to claim 9, wherein said composition further comprises at least one wax.

11. The homogeneous anhydrous make-up cosmetic composition according to claim 1, wherein the composition is a lip composition.

12. The homogeneous anhydrous make-up cosmetic composition according to claim 11, wherein said lip composition is a lipstick.

13. A method of preparing a homogeneous anhydrous make-up cosmetic composition comprising a fatty phase which comprises at least one silicone-containing compound, said method comprising including octyldodecyl neopentanoate in said composition in an amount sufficient to function as a compatibilizing agent, wherein said composition is in the form of a solid or liquid anhydrous greasy product.

14. The method according to claim 13, wherein said homogeneous anhydrous make-up cosmetic composition further comprises at least one wax.

15. A method of preparing an anhydrous make-up product which comprises a homogeneous and anhydrous cosmetic composition comprising at least one silicone-containing compound, said method comprising including octyldodecyl neopentanoate in said homogeneous anhydrous cosmetic composition in an amount sufficient to function as a compatibilizing agent.

16. The method according to claim 15, wherein said anhydrous cosmetic composition further comprises at least one wax.

17. A method for making up the skin, lips, or eyelashes of a human being, comprising applying at least one product to said skin, lips, or eyelashes, wherein said at least one product comprises at least one homogeneous anhydrous cosmetic composition comprising a fatty phase which comprises at least one silicone-containing compound and octyldodecyl neopentanoate.

* * * * *